(12) United States Patent
Tsai et al.

(10) Patent No.: US 11,098,955 B2
(45) Date of Patent: Aug. 24, 2021

(54) MICRO-SCALE WIRELESS HEATER AND FABRICATION METHOD AND APPLICATIONS THEREOF

(71) Applicant: NATIONAL TSING HUA UNIVERSITY, Hsinchu (TW)

(72) Inventors: Hung-Yin Tsai, Hsinchu (TW); Tung Che Lee, New Taipei (TW); Ping Huan Tsai, Taoyuan (TW); Shang Ru Wu, Taichung (TW); Yi Hung Chen, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 477 days.

(21) Appl. No.: 16/256,417

(22) Filed: Jan. 24, 2019

(65) Prior Publication Data
US 2020/0158442 A1 May 21, 2020

(30) Foreign Application Priority Data
Nov. 21, 2018 (TW) .................................. 107141407

(51) Int. Cl.
*F28D 9/00* (2006.01)
*F28F 3/12* (2006.01)
(Continued)

(52) U.S. Cl.
CPC ................ *F28D 9/005* (2013.01); *F28F 3/12* (2013.01); *H01F 27/28* (2013.01); *H02J 50/10* (2016.02)

(58) Field of Classification Search
CPC .. F28D 9/005; F28F 3/12; H01F 27/28; H01F 38/14; H01F 5/003; H01F 17/0006;
(Continued)

(56) References Cited

U.S. PATENT DOCUMENTS 9,370,628 B2 * 6/2016 Takahata ................. A61M 5/44
10,677,647 B2 * 6/2020 Rogers ...................... G01J 1/42
(Continued)

FOREIGN PATENT DOCUMENTS

CN          103596309 A     2/2014
CN          107241821 A    10/2017

*Primary Examiner* — Jared Fureman
*Assistant Examiner* — Michael J Warmflash
(74) *Attorney, Agent, or Firm* — Muncy, Geissler, Olds and Lowe, P.C.

(57) ABSTRACT

A micro-scale wireless heater includes: a support layer having first and second sides and a cavity formed on the second side; a first electrode plate and a first conduction line disposed on the second side; a second electrode plate and a coil both embedded into a slot on the first side, wherein the support layer is disposed between the first and second electrode plates forming a capacitor, the coil forms an inductor, and the slot communicates with the cavity; and a second conduction line disposed in the cavity. The first and second electrode plates are electrically connected together through the first and second conduction lines and the coil in order. Three exposed surfaces of the second electrode plate, the coil and the first side are flush with one another. The inductor and the capacitor convert an electromagnetic wave into heat. A fabrication method and applications thereof are also provided.

10 Claims, 10 Drawing Sheets (51) Int. Cl.
*H01F 27/28* (2006.01)
*H02J 50/10* (2016.01)

(58) Field of Classification Search
CPC ...... H02J 50/10; H01G 4/40; A61F 2007/009;
A61F 7/007; A61N 1/403; H05B 3/03;
H05B 3/02; H05B 3/20
See application file for complete search history.

(56) References Cited

U.S. PATENT DOCUMENTS

| | | | |
|---|---|---|---|
| 2005/0028728 A1* | 2/2005 | Liu | C30B 25/22 |
| | | | 117/86 |
| 2012/0310151 A1 | 12/2012 | Takahata et al. | |
| 2018/0165566 A1 | 6/2018 | Rogers et al. | |

* cited by examiner

MICRO-SCALE WIRELESS HEATER AND FABRICATION METHOD AND APPLICATIONS THEREOF

CROSS-REFERENCE TO RELATED APPLICATIONS

This application claims priority of No. 107141407 filed in Taiwan R.O.C. on Nov. 21, 2018 under 35 USC 119, the entire content of which is hereby incorporated by reference.

BACKGROUND OF THE INVENTION

Field of the Invention

The invention relates to a micro-scale wireless heater and a fabrication method and applications thereof, and more particularly to a micro-scale wireless heater, a fabrication method thereof, and a biological stimulation system and a micro-scale origami system using multiple micro-scale wireless heaters.

Description of the Related Art

With the rapid development of advanced technologies nowadays, the technologies of semiconductor manufacturing and micro-electro-mechanical-system (MEMS) processing rapidly break through. Electronic components are getting smaller and smaller for the purpose of elevating efficiency and saving cost. Therefore, there are more and more functional units located in one system.

U.S. Patent Publication No. US2012/0310151A1 disclosed a wireless microactuator, which can be applied to implantable drug delivery devices, grippers and injectors, provides wireless power and control through frequency tuning of an external radio frequency (RF) magnetic field, and can operate without a battery to provide an actuating function. However, the dimension of the wireless microactuator of the '151 patent is large (e.g., a line width of the coil is about 100 microns, and a gap or pitch is about 150 microns), and the wireless microactuator cannot satisfy the requirement of the more miniature applications. Therefore, there is the considerable requirement and development space for the reduction of wireless microactuator. In addition, the wireless microactuator of the '151 patent uses the polyimide (PI) as the support material, and the contact area between the coil and the support material is small, so that the thermo-conductive effect also needs to be improved.

BRIEF SUMMARY OF THE INVENTION

It is therefore an objective of the invention to provide a micro-scale wireless heater and a fabrication method and applications thereof, wherein the dimension of the micro-scale wireless heater is significantly reduced, the microcrystalline diamond layer is used as the support layer, and a planar coil is embedded into the microcrystalline diamond layer to achieve the high conductive effect.

To achieve the above-identified object, the invention provides a micro-scale wireless heater including: a support layer having a first side, a second side opposite to the first side and a cavity formed on the second side; a first electrode plate and a first conduction line disposed on the second side; a second electrode plate and a coil both embedded into a slot on the first side, wherein the support layer is disposed between the first and second electrode plates, which form a capacitor, the coil forms an inductor, and the slot communicates with the cavity; and a second conduction line disposed in the cavity, wherein the first electrode plate is electrically connected to the second electrode plate through the first conduction line, the second conduction line and the coil in order, three exposed surfaces of the second electrode plate, the coil and the first side of the support layer are flush with one another, and the inductor and the capacitor converts an electromagnetic wave into heat.

In the micro-scale wireless heater, the support layer may be made of a microcrystalline diamond material providing supporting, heat conducting and electrical insulating functions; the second electrode plate and coil may be made of titanium; the second electrode plate, the coil, the first electrode plate, the first conduction line and the second conduction line may be made of titanium; dimensions of the first electrode plate and the second electrode plate may range between 100 microns*300 microns and 1000 microns*500 microns, a line width of the coil may range between 1 micron and 10 microns, and a gap or pitch of the coil may range between 10 microns and 50 microns.

The invention further provides a fabrication method of the micro-scale wireless heater. The method includes the following steps: forming a second metal layer on a semiconductor substrate; patterning the second metal layer to form a second electrode plate and a coil; forming a support layer on and between the second electrode plate and the coil, so that the second electrode plate and the coil are embedded into a slot disposed on a first side of the support layer; forming a cavity on the support layer to expose a portion of the coil; forming a first metal layer in the cavity and on the support layer; patterning the first metal layer to form a first electrode plate and a first conduction line on a second side the support layer, and forming a second conduction line in the cavity; and removing the semiconductor substrate to form the micro-scale wireless heater.

In the fabrication method, the first metal layer in the cavity may form the second conduction line, wherein the support layer is disposed between the first and second electrode plates, which form a capacitor, the coil forms an inductor, and the slot communicates with the cavity, wherein the first electrode plate is electrically connected to the second electrode plate through the first conduction line, the second conduction line and the coil in order, three exposed surfaces of the second electrode plate, the coil and the first side of the support layer are flush with one another, and the inductor and the capacitor receive an electromagnetic wave to generate heat.

The invention also provides a biological stimulation system, which includes: multiple micro-scale wireless heaters respectively disposed on multiple organisms, the micro-scale wireless heaters having different response frequencies; and an electromagnetic wave generator generating multiple electromagnetic waves having frequencies respectively corresponding to the response frequencies to stimulate the organisms respectively and independently. Each of the organisms may be a *drosophila*.

The invention also provides a micro-scale origami system, which includes: a sheet structure having multiple stimulation blocks; multiple micro-scale wireless heaters respectively disposed on the stimulation blocks, the micro-scale wireless heaters having different response frequencies; and an electromagnetic wave generator generating multiple electromagnetic waves having frequencies respectively corresponding to the response frequencies to stimulate the stimulation blocks respectively and independently so that the sheet structure deforms in a specific direction.

With the above-mentioned embodiments, a micro-scale wireless heater can be implemented. Compared with the prior art, the dimension of the micro-scale wireless heater of this embodiment is smaller. The line width of the coil has been reduced to about (1/50), the overall area has also been reduced to about (1/10), and the more miniature dimension is more developmental to the application of micro-electro-mechanical-system. The microcrystalline diamond is used as the heat conducting material in this embodiment, the diamond material has the high thermoconductive property under the micrometer scale to effectively improve the overall system efficiency and uniformity. The microcrystalline diamond film formed by the embodiment is a highly uniform film having the surface roughness Ra equal to about 17 nm only, is sufficient to function as a good support material for titanium metal coils, and provides the uniform thermoconductive effect. Because the dimension is reduced to the micron level, it can be applied to a micro-scale biological stimulation system and a micro-scale origami system, which cannot be achieved by the prior art.

Further scope of the applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In the embodiment of the invention, the electron beam lithography (EBL), reactive-ion etching (RIE) and chemical vapor deposition (CVD) technologies are combined to fabricate the micro-scale wireless heater, and the embodiment becomes more potential in applications.

Figure 1:
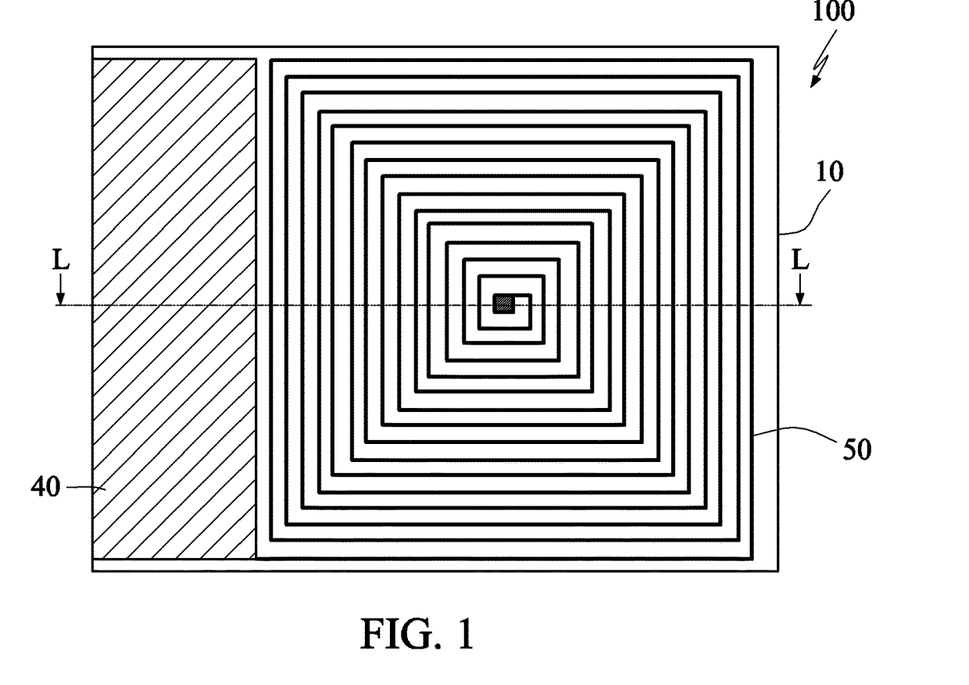
FIGS. 1 and 2 are respectively a bottom view and a top view showing a micro-scale wireless heater according to a preferred embodiment of the invention.
Figure 2:
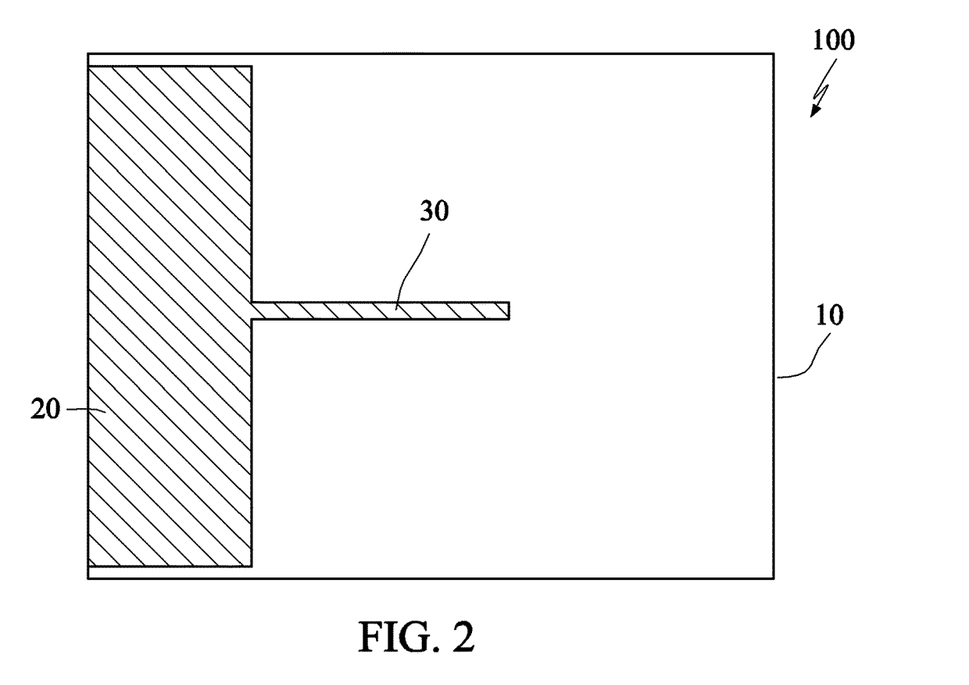
Figures 3, 4A:
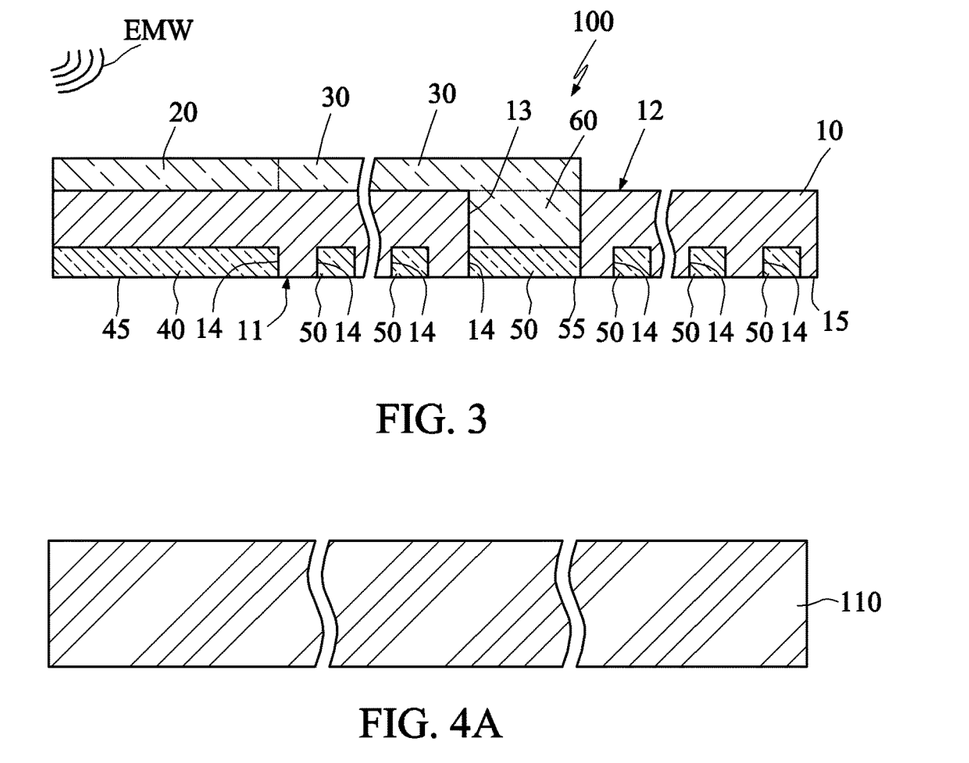
FIG. 3 is a cross-sectional view taken along a line L-L of FIG. 1.
FIGS. 4A to 4R are schematic structure views showing steps of a fabrication method of the micro-scale wireless heater according to the preferred embodiment of the invention.

FIGS. 1 and 2 are respectively a bottom view and a top view showing a micro-scale wireless heater according to a preferred embodiment of the invention. FIG. 3 is a cross-sectional view taken along a line L-L of FIG. 1. As shown in FIGS. 1 to 3, a micro-scale wireless heater 100 of this embodiment includes a support layer 10, a first electrode plate 20, a first conduction line 30, a second electrode plate 40, a coil 50 and a second conduction line 60.

The support layer 10 has a first side 11 and a second side 12 opposite to the first side 11 and a cavity 13, and the cavity 13 is formed on the second side 12. In this embodiment, the support layer 10 is made of a microcrystalline diamond (MCD) providing supporting, heat conducting and electrical insulating functions. The microcrystalline diamond has the high-hardness layer and high thermal conductivity, and is thus quite suitable for the application of this embodiment. A thickness of the support layer 10 ranges between 0.6 microns and 2.8 microns, and is approximately equal to 2 microns in an example.

The first electrode plate 20 and the first conduction line 30 are disposed on the second side 12. For example, the first electrode plate 20 and the first conduction line 30 are located on a plane and are integrally formed to have the same thickness.

The second electrode plate 40 and the coil 50 are embedded into a slot 14 on the first side 11, and the coil 50 is a plane coil. A line width of the coil 50 ranges between 1 micron and 10 microns, and a gap or pitch of the coil 50 ranges between 10 microns and 50 microns. In a non-limiting example, the line width of the coil 50 is equal to 2 microns, and the gap of the coil 50 is equal to 10 microns.

The support layer 10 is disposed between the second electrode plate 40 and the first electrode plate 20, which form a capacitor. The coil 50 forms an inductor, and the slot 14 communicates with the cavity 13. In this embodiment, the second electrode plate 40 and the coil 50 are made of titanium, but they may also be made of any appropriate electroconductive material.

The second conduction line 60 is disposed in the cavity 13. The first electrode plate 20 is electrically connected to the second electrode plate 40 through the first conduction line 30, the second conduction line 60 and the coil 50 in order. In this embodiment, the first electrode plate 20, the first conduction line 30 and the second conduction line 60 are integrally formed. In addition, three exposed surfaces 45, 55 and 15 of the second electrode plate 40, the coil 50 and the first side 11 of the support layer 10 are flush with one another (disposed at the same level or on the same horizontal plane). Therefore, embedding the second electrode plate 40 and the coil 50 into the support layer 10 may further increase the structural strength of the micro-scale wireless heater 100. In addition, because the coil 50 and the second electrode plate 40 are embedded into the support layer 10, a contact area of the coil 50 and the second electrode plate 40 contacting the support layer 10 becomes larger, and this is advantageous to heat conductivity to achieve fast response.

In the practical application, the inductor and the capacitor receive and convert an electromagnetic wave EMW into heat. In a non-limiting example, the second electrode plate 40, the coil 50, the first electrode plate 20, the first conduction line 30 and the second conduction line 60 are made of titanium.

Dimensions of the first electrode plate 20 and the second electrode plate 40 range between 100 microns*300 microns and 1,000 microns*500 microns. In one example, the dimensions of the first electrode plate 20 and the second electrode plate 40 equal to 100 microns*300 microns, and the area covered by the second electrode plate 40 and the coil 50 is equal to 410 microns*300 microns.

Figure 4B:
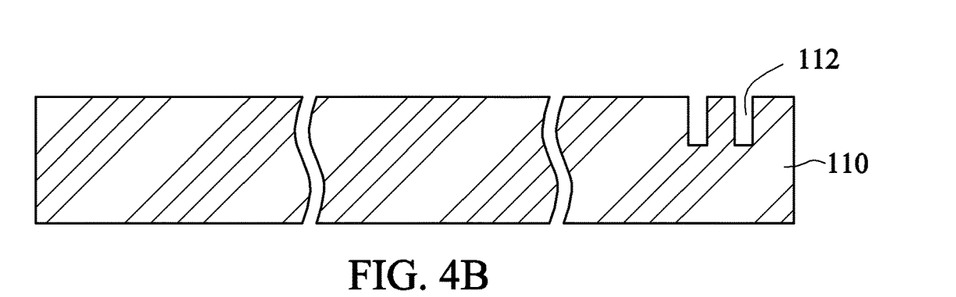
Figure 4C:
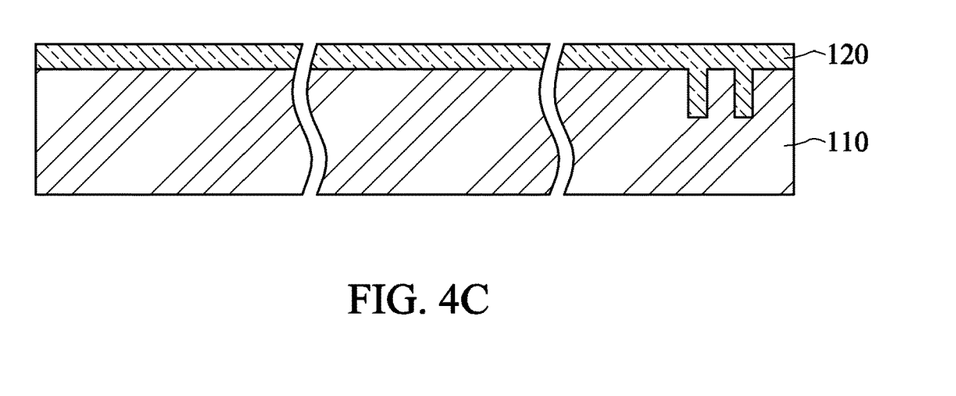
Figure 4D:
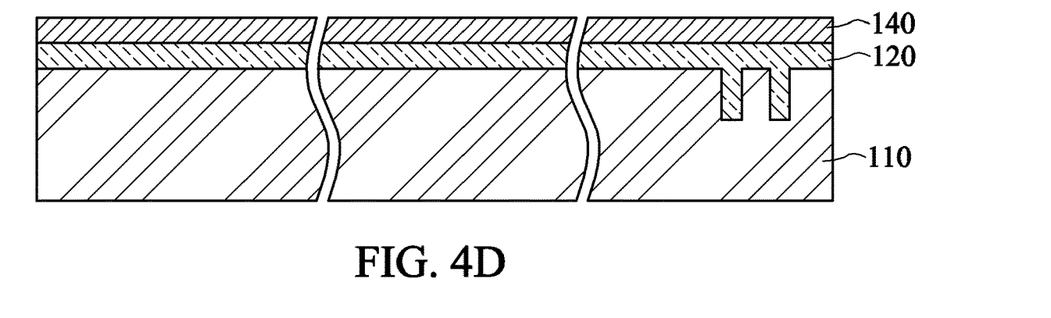
Figure 4E:
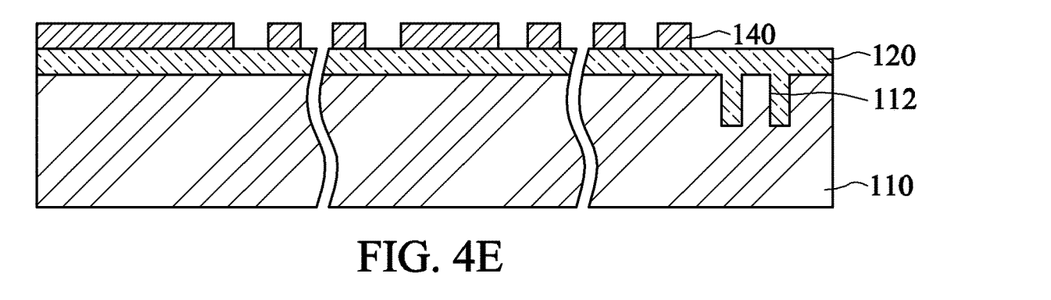
Figure 4F:
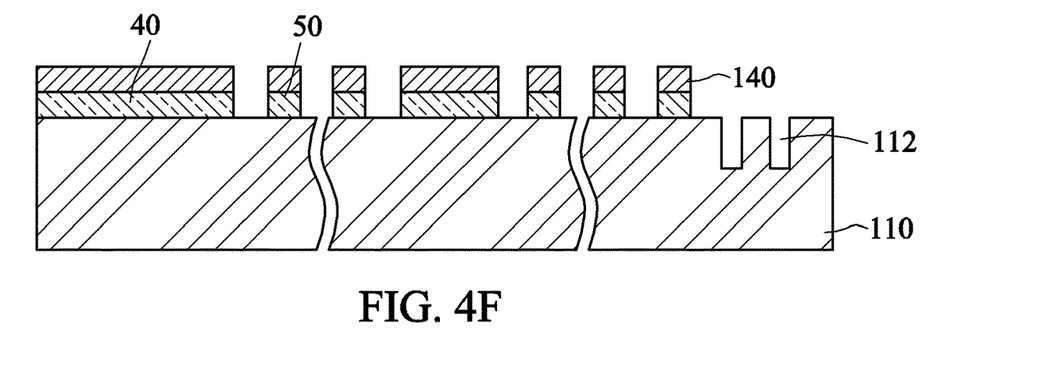
Figure 4G:
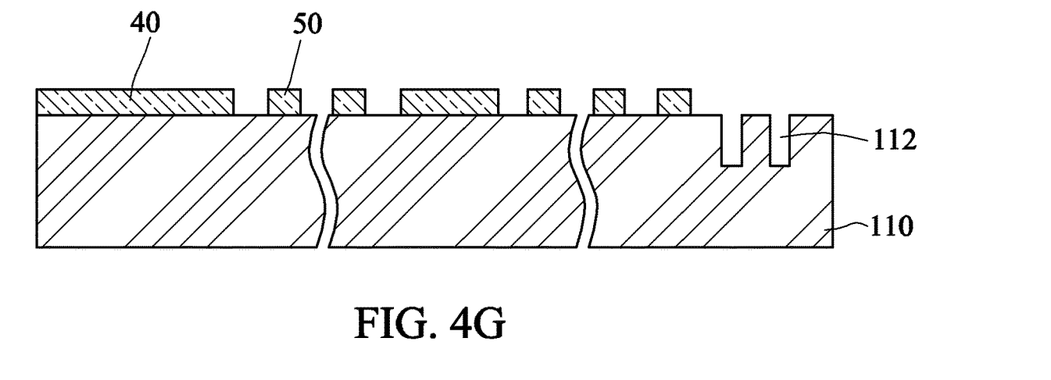
Figure 4H:
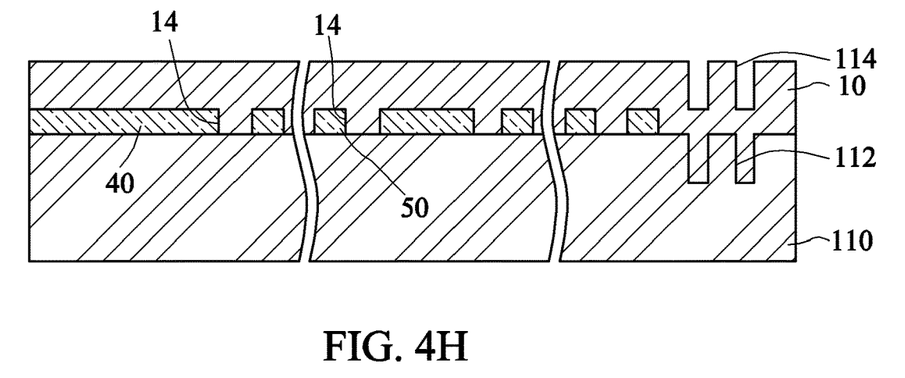
Figure 4I:
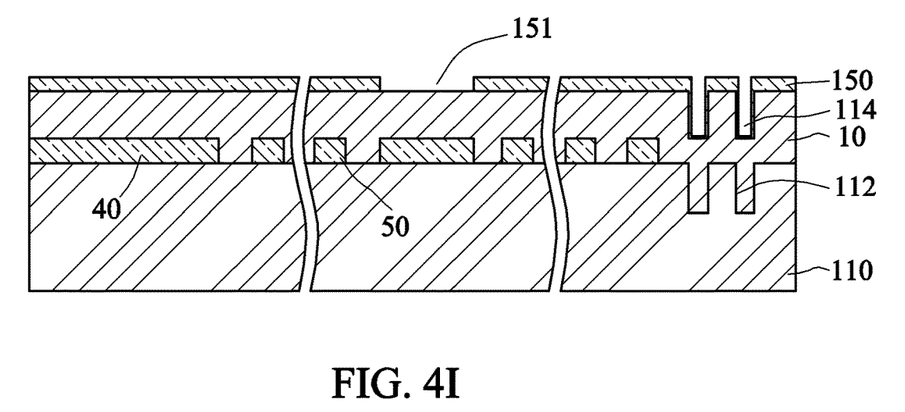
Figure 4J:
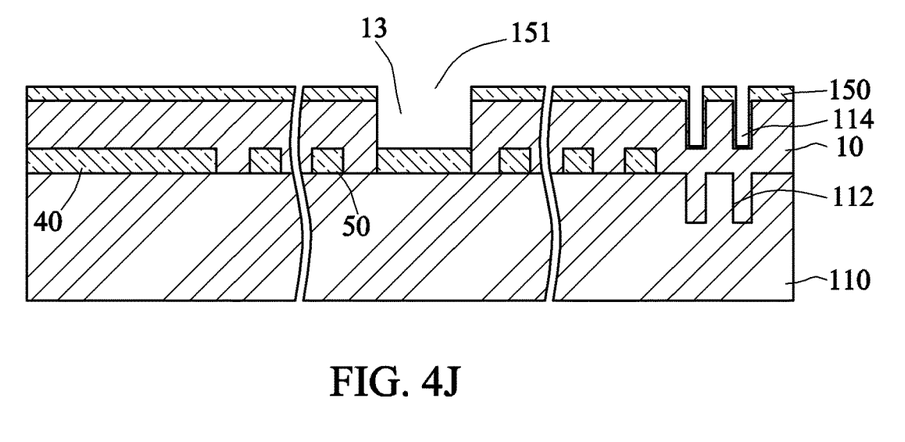
Figure 4K:
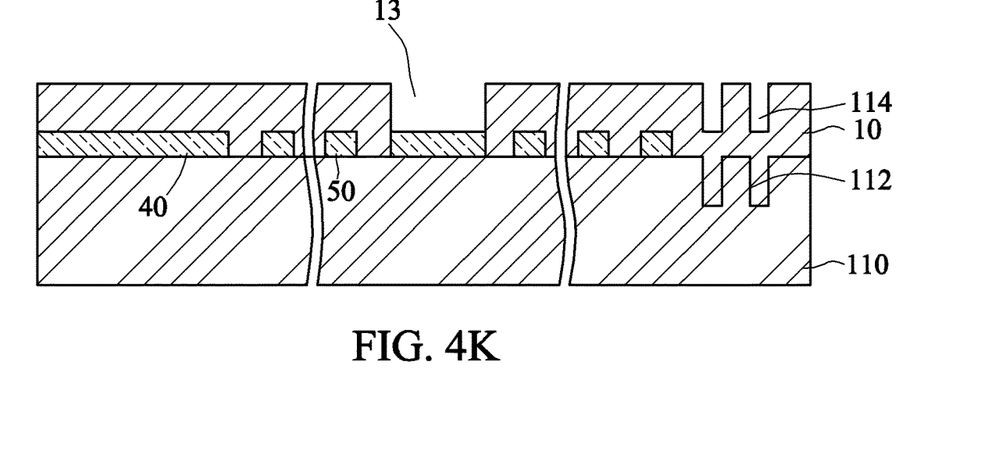
Figure 4L:
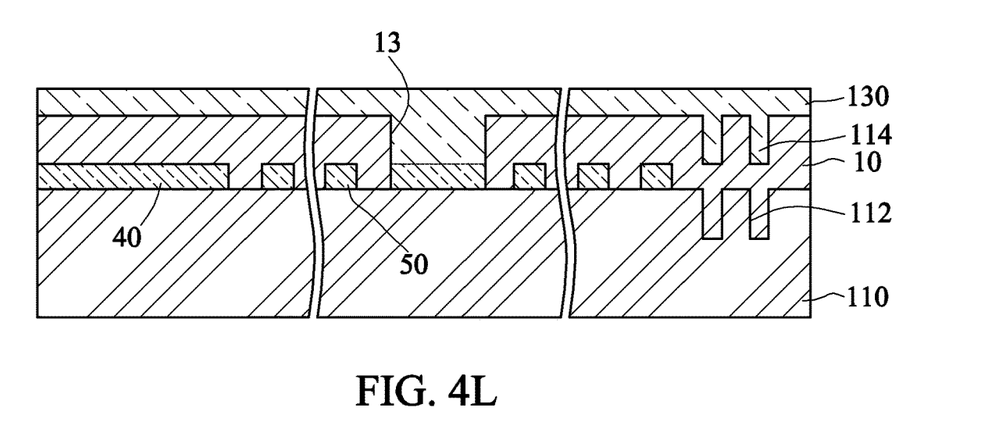
Figure 4M:
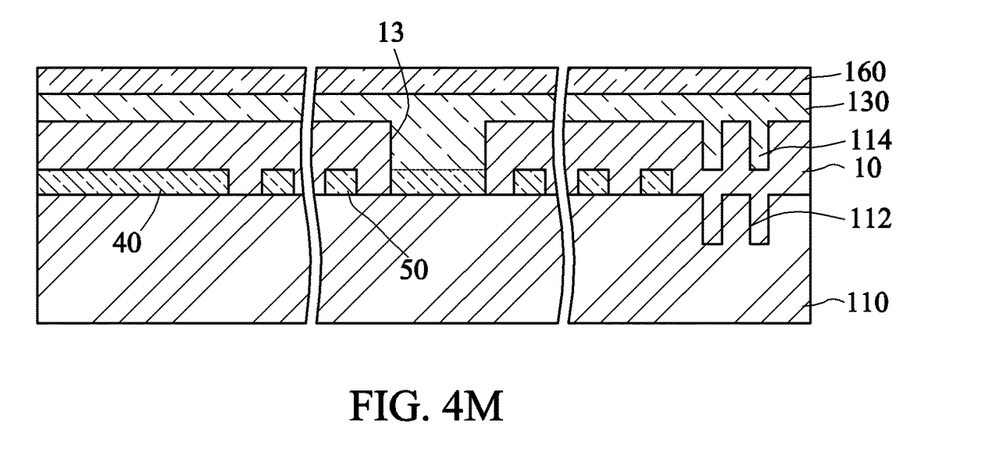
Figure 4N:
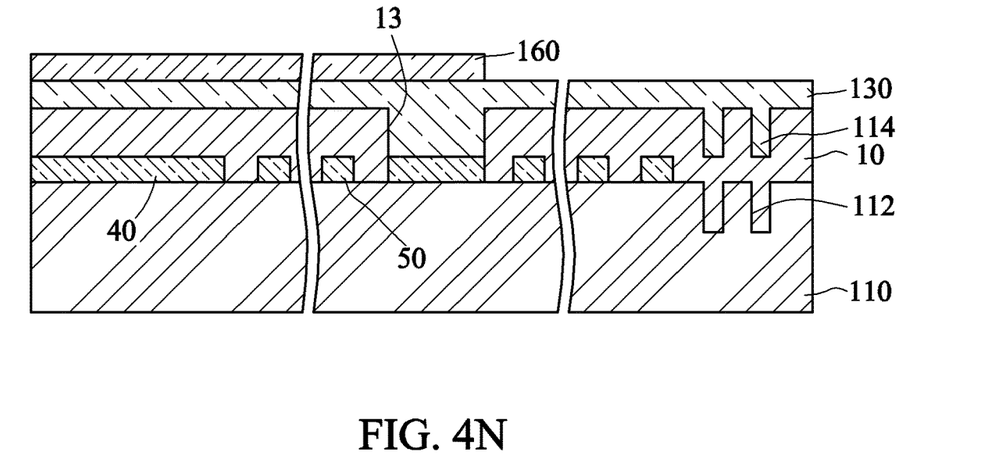
Figure 4O:
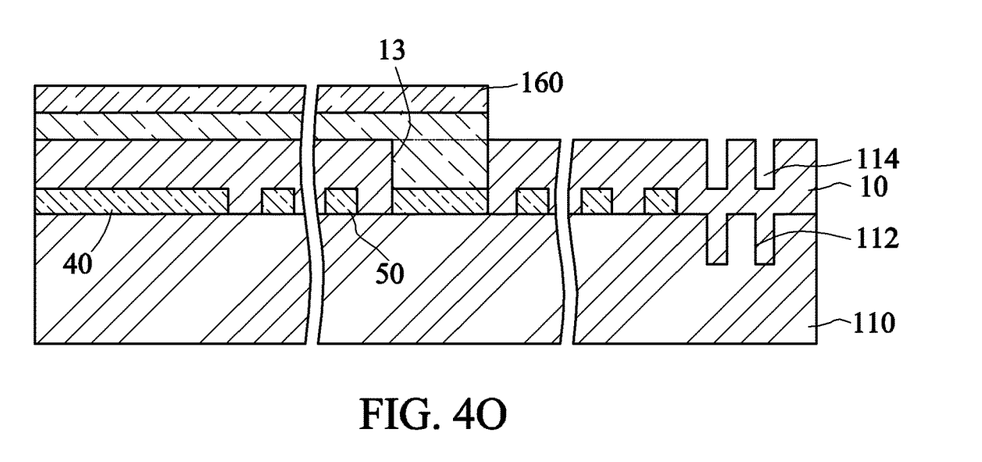
Figure 4P:
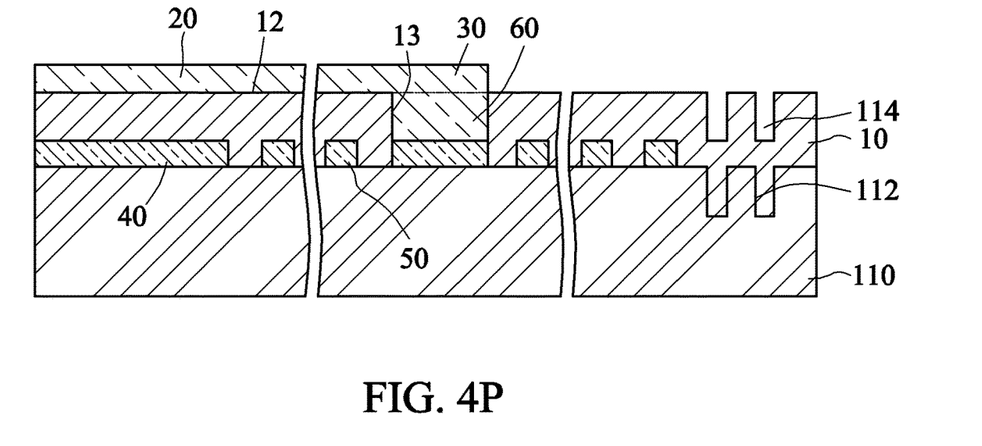
Figure 4Q:
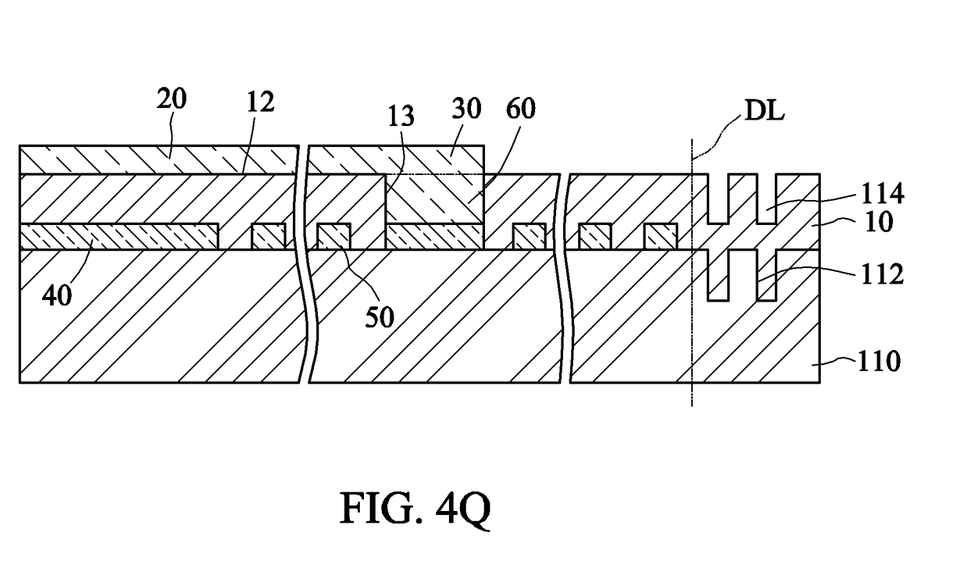
Figure 4R:
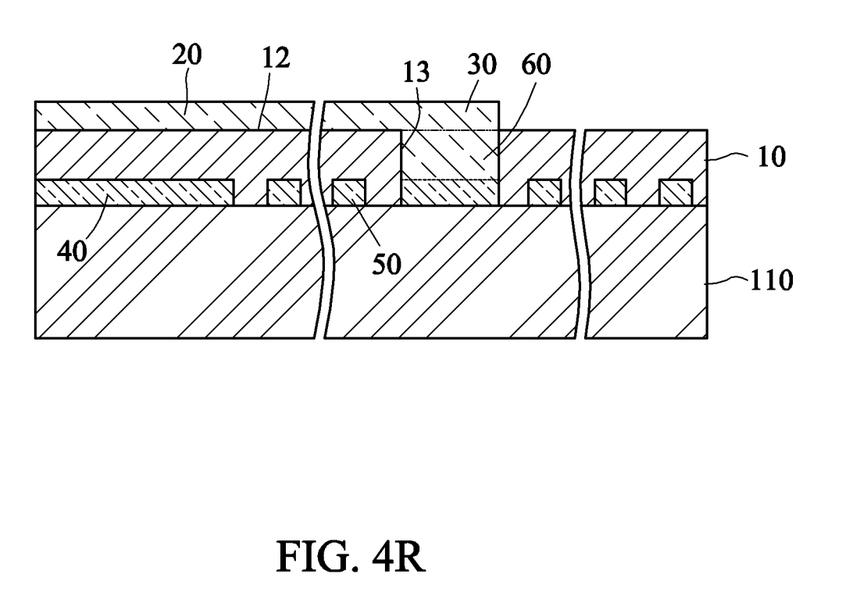

FIGS. 4A to 4R are schematic structure views showing steps of a fabrication method of the micro-scale wireless heater according to the preferred embodiment of the invention. The numerical values of the dimensions described below are merely illustrative and the invention is not limited thereto. In addition, multiple micro-scale wireless heaters arranged in an array may be made at a time, and then the independent micro-scale wireless heaters are produced by way of dicing. For simplicity, the single micro-scale wireless heater is taken as an example for explanation in the following.

The fabrication method of the micro-scale wireless heater includes the following steps. As shown in FIGS. 4A to 4C, a second metal layer 120 is formed on a semiconductor substrate 110. Specifically speaking, the semiconductor substrate 110, such as a silicon substrate having a thickness of 300 microns, is provided firstly, as shown in FIG. 4A. Then, a positioning hole 112 or a positioning pattern is etched on the semiconductor substrate 110 by way of photo-lithography, as shown in FIG. 4B. For example, a photoresist is coated and then patterned, the photo-lithography technology is performed, and then the photoresist is removed. Next, as shown in FIG. 4C, the second metal layer 120 is deposited in the positioning hole 112 and on the semiconductor substrate 110, the material of the second metal layer 120 is, for example, titanium (may also be any other suitable metal material), and the thickness of the second metal layer 120 on the semiconductor substrate 110 is about 300 nanometers (nm).

Then, as shown in FIGS. 4D to 4G, the second metal layer 120 is patterned to form a second electrode plate 40 and a coil 50. Specifically speaking, as shown in FIG. 4D, a resist layer 140 is formed on the second metal layer 120. Next, as shown in FIG. 4E, the resist layer 140 is patterned according to the positioning hole 112. For example, the electron beam lithography is used to define the pattern of the resist layer. Then, as shown in FIG. 4F, the patterned resist layer 140 is taken as a mask to etch the second metal layer 120 to form the second electrode plate 40 and the coil 50. Next, as shown in FIG. 4G, the resist layer 140 is removed.

Then, as shown in FIG. 4H, a support layer 10 is formed on and between the second electrode plate 40 and the coil 50, so that the second electrode plate 40 and the coil 50 are embedded into a slot 14 disposed on a first side 11 of the support layer 10, wherein a portion corresponding to the positioning hole 112 also forms a positioning hole 114. The support layer 10 is a uniform micron crystallization diamond film formed by way of chemical vapor deposition, for example.

Next, as shown in FIGS. 4I to 4K, a cavity 13 is formed on the support layer 10, so that a portion of the coil 50 is exposed. Specifically speaking, as shown in FIG. 4I, a patterned mask layer 150 is formed on the support layer 10 and in the positioning hole 114. The material of the mask layer 150 is, for example, aluminum, but any other suitable material may also be used. For example, an aluminum layer is deposited firstly, the photoresist and photo-lithography technologies are adopted, and a patterned aluminum layer (having a through hole 151) is formed based on the positioning hole 112, so that a portion of the support layer 10 is exposed. Then, as shown in FIG. 4J, the support layer 10 is etched (e.g. by way of anisotropic etching of reactive ion etching) by taking the patterned mask layer 150 as a mask to form the cavity 13 to expose a portion of the coil 50. Next, as shown in FIG. 4K, the mask layer 150 is removed.

Then, as shown in FIG. 4L, a first metal layer 130 is formed on the cavity 13 and the support layer 10. The material of the first metal layer 130 is, for example, titanium (may also be other suitable metal materials), and the thickness of the first metal layer 130 on the support layer 10 is equal to 500 nm, for example.

Next, as shown in FIGS. 4M to 4Q, the first metal layer 130 is patterned to form a first electrode plate 20 and a first conduction line 30 on a second side 12 of the support layer 10, and to form a second conduction line 60 in the cavity 13 (the first metal layer 130 in the cavity 13 forms the second conduction line 60). Specifically speaking, as shown in FIG. 4M, a resist layer 160 is formed on the first metal layer 130. Then, as shown in FIG. 4N, for example, the electron beam lithography is used to pattern the resist layer 160 to expose a portion of the first metal layer 130. Next, as shown in FIG. 4O, the patterned resist layer 160 is used as a mask, and the first metal layer 130 is etched based on the positioning hole 112, and the etch stops on the support layer 10. Then, as shown in FIG. 4P, the resist layer 160 is removed. The second conduction line 60 and the first conduction line 30 are integrally formed with the same material. Next, as shown in FIG. 4Q, cutting is performed along the scribing line DL to form the structure of FIG. 4R.

Then, as shown in FIGS. 4R and 3, the semiconductor substrate 110 is removed, and the above-mentioned micro-scale wireless heater 100 is formed.

Therefore, the micro-scale wireless heater is designed according to the MEMS process technology in this embodiment, and the heater is composed of the inductor and the capacitor. In an example, the dimension of the titanium metal capacitor is 100*300 microns, the inductor is composed of the titanium metal coil having the line width of 2 microns and the pitch of 10 microns, and the microcrystalline diamond (MCD) layer is taken as a support material to provide the structural strength and thermal conductivity. The heater of this design uses the electromagnetic waves as an energy source to achieve the remote control of the temperature in a wireless manner, and the required response frequency can be changed by changing the dimensions of the capacitor and the inductor, so that the temperatures of individual heaters can be wirelessly controlled by different electromagnetic wave frequencies.

Figure 5A:
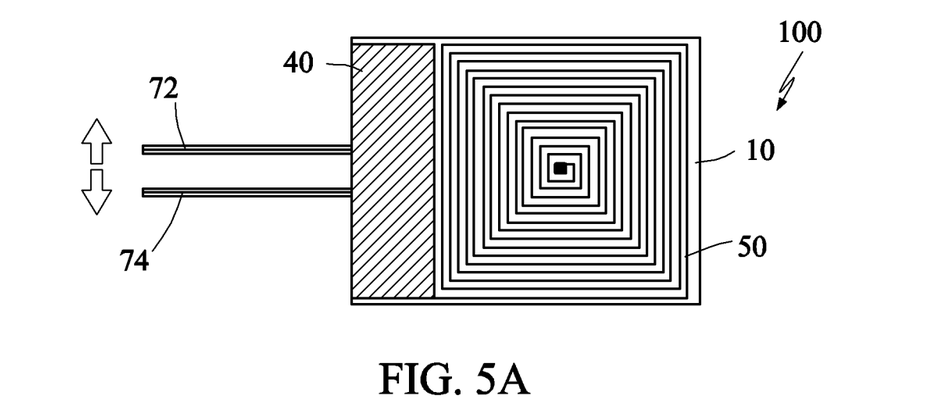
FIGS. 5A and 5B are two examples showing the application of the micro-scale wireless heater.
Figure 5B:
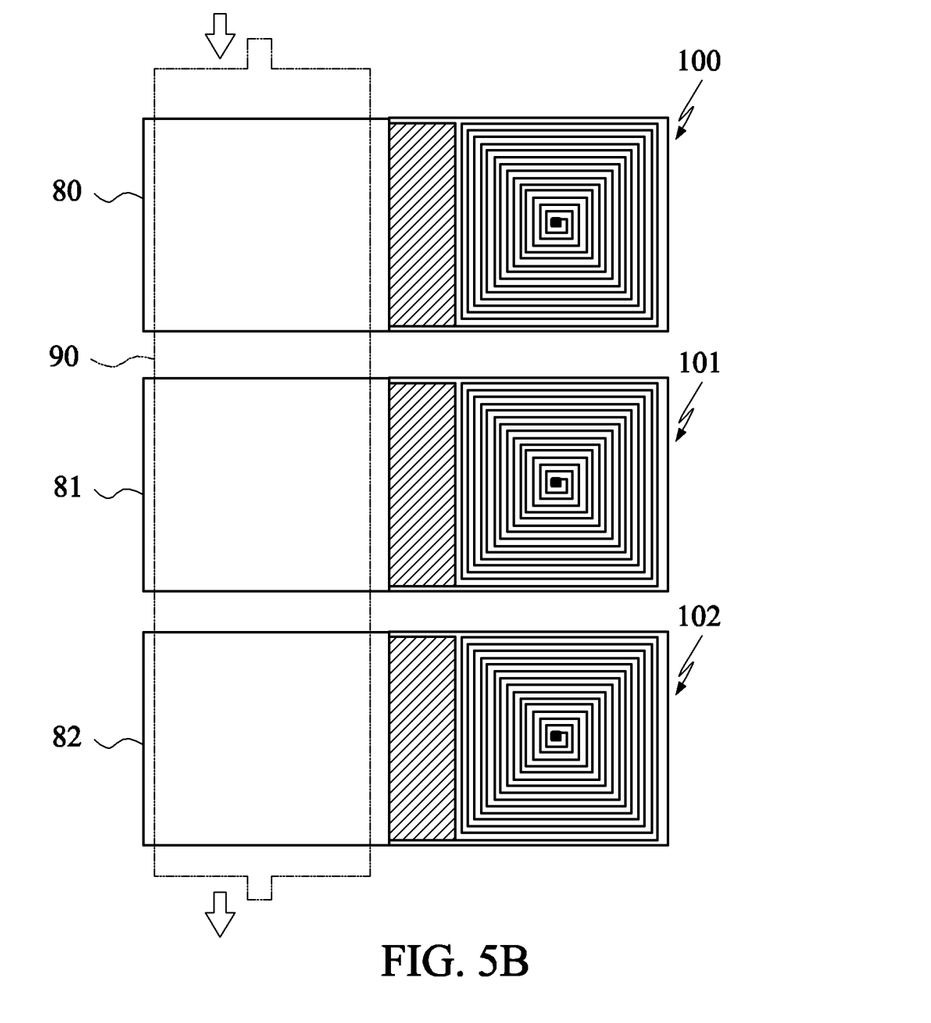

FIGS. 5A and 5B are two examples showing the application of the micro-scale wireless heater. Two arms 72 and 74 of the micro-scale fixture are heated by the micro-scale wireless heater of this embodiment. The bending directions of the two arms 72 and 74 may be controlled by the difference in the expansion coefficients of the composite materials of the arms 72 and 74 so that the opening of the gripper composed by the arms 72 and 74 can be controlled, and the wireless micro-scale fixture can be fabricated, as shown in FIG. 5A. The arms 72 and 74 may be directly connected to the second electrode plate 40, the support layer 10 or the first electrode plate. FIG. 5B is a schematic view showing a wireless microfluidic control system, wherein multiple sets of the combination of the micro-scale wireless heaters 100 to 102 and cantilever beams 80 to 82 are used, and the degree of warpage of one single or multiple sets of cantilever beams 80 to 82 may be controlled by one single or multiple sets of electromagnetic waves of the specific wavelength to press a fluid reservoir 90 (e.g., in a direction toward the location under the drawing sheet), thereby controlling the flow of the entire microfluidic system. For example, pressing the fluid reservoir 90 by the cantilever beams 80 to 82 in order allows the fluid to flow in the direction indicated by the arrow, and controlling different pressing amounts can control the flow.

Figure 6:
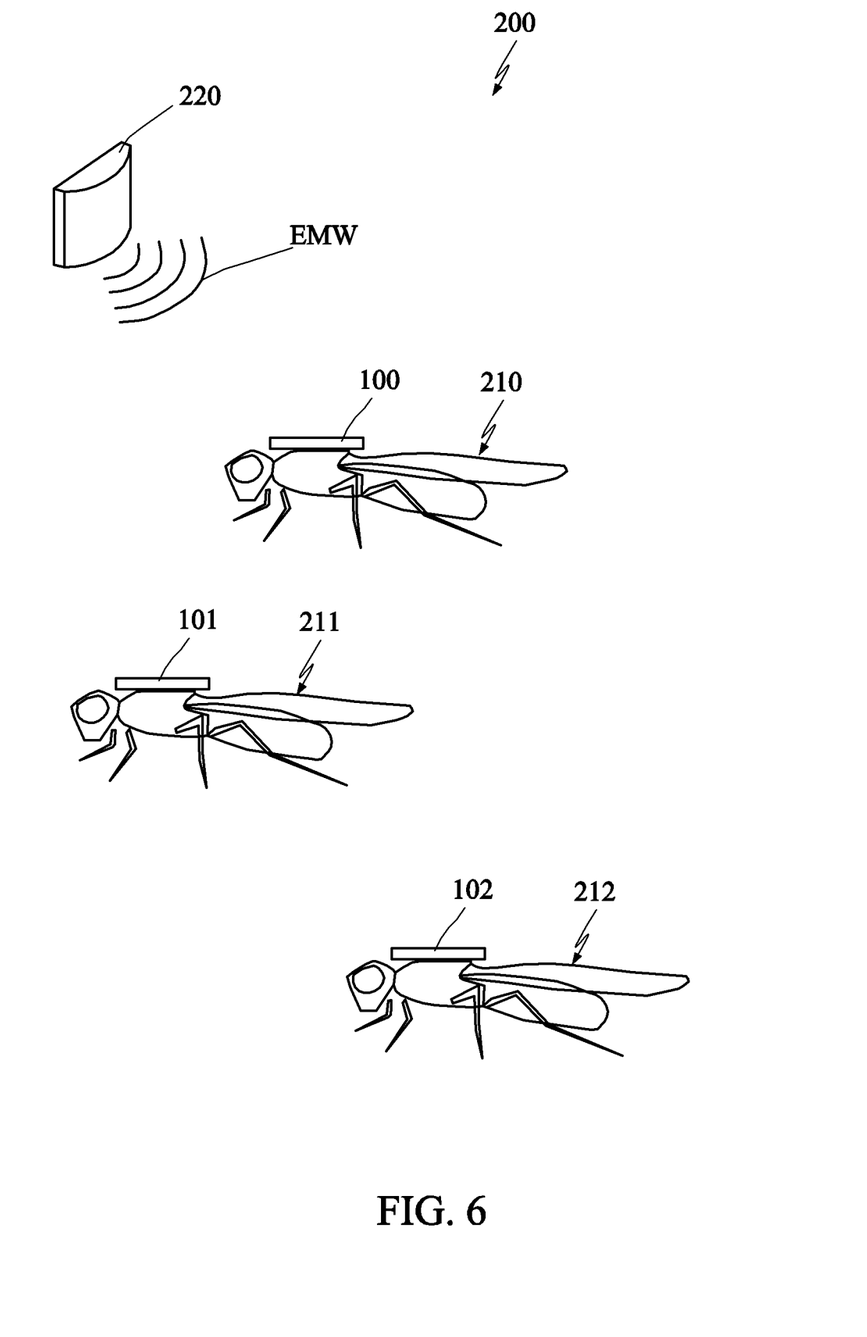
FIG. 6 is a schematic view showing a biological stimulation system applying multiple micro-scale wireless heaters.

FIG. 6 is a schematic view showing a biological stimulation system 200 applying multiple micro-scale wireless heaters. In model biological experiments, because the brain structure of a *drosophila* is highly similar to that of the mammal, the *drosophila* is often used as brain science researches to explore human-related diseases, neurotransmitter systems, biological evolution and the like. One single drosophila is very tiny (about 3.5 mm long, 1.5 mm wide and 1.5 mm high) and light (about 0.5 to 1 mg), so it is necessary to fabricate the advanced MEMS devices for biological experiments. The dimension of the micro-scale wireless heating coil of this embodiment is small enough to be placed on a single *drosophila*, wherein the externally applied electromagnetic waves are provided to the heaters, which convert waves into heat. With the designs of the dimensions of the coils, the *drosophilae* can be properly stimulated. Referring to FIG. 6, the biological stimulation system 200 includes: multiple micro-scale wireless heaters 100 to 102 respectively disposed on multiple organisms 210 to 212, wherein the micro-scale wireless heaters 100 to 102 have different response frequencies; and an electromagnetic wave generator 220 generating multiple electromagnetic waves EMW having frequencies respectively corresponding to the response frequencies to stimulate the organisms 210 to 212 respectively and independently. Each of the organisms 210 to 212 may be a *drosophila*, for example. Multiple electromagnetic wave generators each generating the electromagnetic wave having one single frequency may also be synthesized into a single electromagnetic wave generator that can generate multiple electromagnetic waves.

Figure 7:
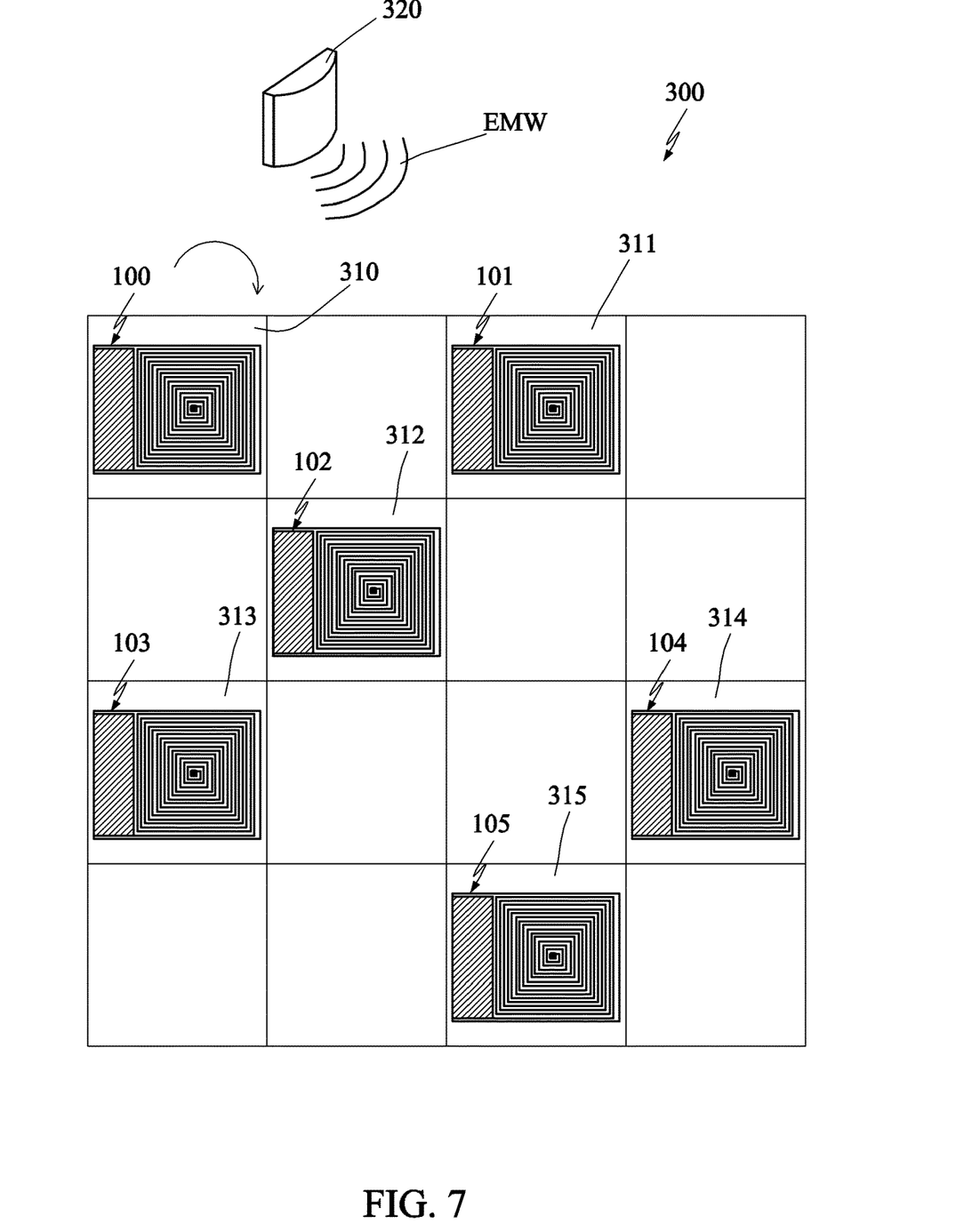
FIG. 7 is a schematic view showing a micro-scale origami system applying multiple micro-scale wireless heaters.

FIG. 7 is a schematic view showing a micro-scale origami system 300 applying multiple micro-scale wireless heaters. Using the micro-scale wireless heater of this embodiment combined with the origami science process, the shape memory material can be controlled by electromagnetic waves to control the deformation of the single or multiple regions of the component. The wireless coils may be heated through different bands of electromagnetic waves to control the deformation of a specific area in a specified direction. This concept can be derived into many fields of applications, such as the aerospace technology, biomedical researches, communication applications, energy technology, electromechanical systems, robotics or the like. Referring to FIG. 7, the micro-scale origami system 300 includes: a sheet structure 310 having multiple stimulation blocks 310 to 315; multiple micro-scale wireless heaters 100 to 105 respectively disposed on the stimulation blocks 310 to 315, the micro-scale wireless heaters 100 to 105 having different response frequencies; and an electromagnetic wave generator 320 generating multiple electromagnetic waves EMW having frequencies respectively corresponding to the response frequencies to provide stimulation (e.g., heating stimulation) to the stimulation blocks 310 to 315 respectively and independently so that the sheet structure 310 deforms in a specific direction. The sheet structure 310 is formed by shape memory materials, for example.

With the above-mentioned embodiments, a micro-scale wireless heater can be implemented. Compared with the prior art, the dimension of the micro-scale wireless heater of this embodiment is smaller. The line width of the coil has been reduced to about (1/50), the overall area has also been reduced to about (1/10), and the more miniature dimension is more developmental to the application of micro-electromechanical-system. The microcrystalline diamond is used as the heat conducting material in this embodiment, the diamond material has the high thermoconductive property under the micrometer scale to effectively improve the overall system efficiency and uniformity. The microcrystalline diamond film formed by the embodiment is a highly uniform film having the surface roughness Ra equal to about 17 nm only, is sufficient to function as a good support material for titanium metal coils, and provides the uniform thermoconductive effect. Because the dimension is reduced to the micron level, it can be applied to a micro-scale biological stimulation system and a micro-scale origami system, which cannot be achieved by the prior art.

While the invention has been described by way of examples and in terms of preferred embodiments, it is to be understood that the invention is not limited thereto. To the contrary, it is intended to cover various modifications. Therefore, the scope of the appended claims should be accorded the broadest interpretation so as to encompass all such modifications.

What is claimed is:

1. A micro-scale wireless heater, comprising:
   a support layer having a first side, a second side opposite to the first side and a cavity formed on the second side;
   a first electrode plate and a first conduction line disposed on the second side;
   a second electrode plate and a coil both embedded into a slot on the first side, wherein the support layer is disposed between the second electrode plate and the first electrode plate, which form a capacitor, the coil forms an inductor, and the slot communicates with the cavity; and
   a second conduction line disposed in the cavity, wherein the first electrode plate is electrically connected to the second electrode plate through the first conduction line, the second conduction line and the coil in order, three exposed surfaces of the second electrode plate, the coil and the first side of the support layer are flush with one another, and the inductor and the capacitor converts an electromagnetic wave into heat.

2. The micro-scale wireless heater according to claim 1, wherein the support layer is made of a microcrystalline diamond material providing supporting, heat conducting and electrical insulating functions.

3. The micro-scale wireless heater according to claim 1, wherein the second electrode plate and the coil are made of titanium.

4. The micro-scale wireless heater according to claim 1, wherein the second electrode plate, the coil, the first electrode plate, the first conduction line and the second conduction line are made of titanium.

5. The micro-scale wireless heater according to claim 1, wherein dimensions of the first electrode plate and the second electrode plate range between 100 microns*300 microns and 1000 microns*500 microns, a line width of the coil ranges between 1 micron and 10 microns, and a pitch of the coil ranges between 10 microns and 50 microns.

6. A biological stimulation system, comprising:
   multiple micro-scale wireless heaters each according to claim 1 respectively disposed on multiple organisms, the micro-scale wireless heaters having different response frequencies; and
   an electromagnetic wave generator generating multiple electromagnetic waves having frequencies respectively corresponding to the response frequencies to stimulate the organisms respectively and independently.

7. The biological stimulation system according to claim 6, wherein each of the organisms is a *drosophila*.

8. A micro-scale origami system, comprising:
   a sheet structure having multiple stimulation blocks;
   multiple micro-scale wireless heaters each according to claim 1 respectively disposed on the stimulation blocks, the micro-scale wireless heaters having different response frequencies; and
   an electromagnetic wave generator generating multiple electromagnetic waves having frequencies respectively corresponding to the response frequencies to stimulate the stimulation blocks respectively and independently so that the sheet structure deforms in a specific direction.

9. A fabrication method of a micro-scale wireless heater, comprising steps of:

forming a second metal layer on a semiconductor substrate;

patterning the second metal layer to form a second electrode plate and a coil;

forming a support layer on and between the second electrode plate and the coil, so that the second electrode plate and the coil are embedded into a slot disposed on a first side of the support layer;

forming a cavity on the support layer to expose a portion of the coil;

forming a first metal layer in the cavity and on the support layer;

patterning the first metal layer to form a first electrode plate and a first conduction line on a second side of the support layer, and forming a second conduction line in the cavity; and removing the semiconductor substrate to form the micro-scale wireless heater.

10. The fabrication method according to claim 9, wherein the first metal layer in the cavity forms the second conduction line, the support layer is disposed between the second electrode plate and the first electrode plate, which form a capacitor, the coil forms an inductor, the slot communicates with the cavity, the first electrode plate is electrically connected to the second electrode plate through the first conduction line, the second conduction line and the coil in order, three exposed surfaces of the second electrode plate, the coil and the first side of the support layer are flush with one another, and the inductor and the capacitor convert an electromagnetic wave into heat.

* * * * *